US010010398B2

(12) United States Patent
Treloar et al.

(10) Patent No.: US 10,010,398 B2
(45) Date of Patent: Jul. 3, 2018

(54) FILTER DEVICE, SYSTEM, AND METHOD (71) Applicant: COOK MEDICAL TECHNOLOGIES LLC, Bloomington, IN (US)

(72) Inventors: Thomas Adam Treloar, Loveland, OH (US); Leslie Cook, Indianapolis, IN (US); John Tyler Strader, Elizabethtown, KY (US); Nathan Kemper, Crestline, OH (US); Don Patterson, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 480 days.

(21) Appl. No.: 14/503,860

(22) Filed: Oct. 1, 2014

(65) Prior Publication Data

US 2015/0094754 A1 Apr. 2, 2015

Related U.S. Application Data (60) Provisional application No. 61/885,210, filed on Oct. 1, 2013.

(51) Int. Cl.
A61F 2/01 (2006.01)

(52) U.S. Cl.
CPC ........... *A61F 2/01* (2013.01); *A61F 2002/011* (2013.01); *A61F 2210/0014* (2013.01); *A61F 2220/0016* (2013.01)

(58) Field of Classification Search
CPC .............................. A61F 2/01; A61F 2002/011; A61F 2002/016; A61F 2002/018
See application file for complete search history.

(56) References Cited

U.S. PATENT DOCUMENTS

| 4,425,908 | A |   | 1/1984 | Simon |
|-----------|---|---|--------|-------|
| 5,133,733 | A | * | 7/1992 | Rasmussen ............... A61F 2/01 606/200 |
| 5,324,304 | A | * | 6/1994 | Rasmussen ............... A61F 2/01 128/899 |
| 5,344,427 | A | * | 9/1994 | Cottenceau ............... A61F 2/01 606/200 |

(Continued)

FOREIGN PATENT DOCUMENTS

| EP | 2459119 A1 | 6/2012 |
|----|------------|--------|
| EP | 2536461 A2 | 12/2012 |

(Continued)

*Primary Examiner* — David C Eastwood
(74) *Attorney, Agent, or Firm* — Brinks Gilson & Lione (57) ABSTRACT A filter device has a single hub and a plurality of filter struts extending in a first longitudinal direction. A plurality of wire loops extend in a second longitudinal direction opposite the filter struts. The filter struts and wire loops each engage the vessel wall of a body lumen when deployed. The wire loops limit the filter device from becoming tilted and embedded in the vessel wall. A retrieval device includes a sheath and a snaring mechanism. The snaring mechanism engages a hook member of the filter and the sheath envelopes the wire loops and filter struts. The sheath will cause the wire loops to bend and fold over the filter struts during retrieval such that the wire loops and filter struts extend in the same longitudinal direction after being enveloped by the sheath.

15 Claims, 7 Drawing Sheets

(56) References Cited

U.S. PATENT DOCUMENTS

| | | | | |
|---|---|---|---|---|
| 5,634,942 A | * | 6/1997 | Chevillon | A61F 2/01 606/194 |
| 5,853,420 A | * | 12/1998 | Chevillon | A61F 2/01 606/194 |
| 6,126,673 A | | 10/2000 | Kim et al. | |
| 6,391,045 B1 | | 5/2002 | Kim et al. | |
| 6,872,217 B2 | * | 3/2005 | Walak | A61F 2/01 606/200 |
| 7,128,752 B2 | | 10/2006 | Bales | |
| 7,150,756 B2 | | 12/2006 | Levinson et al. | |
| 7,169,166 B2 | | 1/2007 | Richter | |
| 7,179,274 B2 | | 2/2007 | Bruckheimer et al. | |
| 7,179,275 B2 | | 2/2007 | McGuckin, Jr. et al. | |
| 7,214,237 B2 | | 5/2007 | Don Michael et al. | |
| 7,226,464 B2 | | 6/2007 | Garner et al. | |
| 7,229,462 B2 | | 6/2007 | Sutton et al. | |
| 7,229,463 B2 | | 6/2007 | Sutton et al. | |
| 7,229,464 B2 | | 6/2007 | Hanson et al. | |
| 7,244,267 B2 | | 7/2007 | Huter et al. | |
| 7,261,731 B2 | | 8/2007 | Patel et al. | |
| 7,279,000 B2 | | 10/2007 | Cartier et al. | |
| 7,306,619 B1 | | 12/2007 | Palmer | |
| 7,314,477 B1 | | 1/2008 | Ravenscroft et al. | |
| 7,323,002 B2 | | 1/2008 | Johnson et al. | |
| 7,338,512 B2 | | 3/2008 | McGuckin, Jr. et al. | |
| 7,399,308 B2 | | 7/2008 | Borillo et al. | |
| 7,479,151 B2 | | 1/2009 | Rosenschein et al. | |
| 7,479,153 B2 | | 1/2009 | Belef | |
| 7,481,823 B2 | | 1/2009 | Broome et al. | |
| 7,491,215 B2 | | 2/2009 | Vale et al. | |
| 7,491,216 B2 | | 2/2009 | Brady | |
| 7,534,251 B2 | | 5/2009 | WasDyke et al. | |
| 7,544,202 B2 | | 6/2009 | Cartier et al. | |
| 7,575,584 B2 | | 8/2009 | WasDyke | |
| 7,585,309 B2 | | 9/2009 | Larson | |
| 7,618,433 B2 | | 11/2009 | Daniel et al. | |
| 7,625,390 B2 | | 12/2009 | Hendriksen et al. | |
| 7,648,518 B2 | | 1/2010 | Salahieh et al. | |
| 7,686,825 B2 | | 3/2010 | Hauser et al. | |
| 7,699,867 B2 | | 4/2010 | Hendriksen et al. | |
| 7,704,266 B2 | * | 4/2010 | Thinnes, Jr. | A61F 2/01 606/200 |
| 7,704,267 B2 | | 4/2010 | Tessmer | |
| 7,717,935 B2 | | 5/2010 | Tsugita et al. | |
| 7,722,635 B2 | | 5/2010 | Beyer et al. | |
| 7,731,722 B2 | | 6/2010 | Lavelle et al. | |
| 7,749,246 B2 | | 7/2010 | McGuckin, Jr. et al. | |
| 7,758,606 B2 | | 7/2010 | Streeter et al. | |
| 7,763,045 B2 | | 7/2010 | Osborne | |
| 7,766,932 B2 | | 8/2010 | Melzer et al. | |
| 7,785,343 B2 | | 8/2010 | Johnson et al. | |
| 7,794,472 B2 | | 9/2010 | Eidenschink et al. | |
| 7,803,171 B1 | | 9/2010 | Uflacker | |
| 7,806,906 B2 | | 10/2010 | Don Michael | |
| 7,854,747 B2 | | 12/2010 | Johnson et al. | |
| 7,862,578 B2 | | 1/2011 | Tsugita | |
| 7,875,051 B2 | | 1/2011 | Beulke et al. | |
| 7,879,063 B2 | | 2/2011 | Khosravi | |
| 7,879,065 B2 | | 2/2011 | Gesswein et al. | |
| 7,887,561 B2 | | 2/2011 | McGuckin, Jr. et al. | |
| 7,896,898 B2 | | 3/2011 | WasDyke | |
| 7,901,427 B2 | | 3/2011 | Brady | |
| 7,909,847 B2 | | 3/2011 | McGuckin, Jr. et al. | |
| 7,931,665 B2 | | 4/2011 | Tsugita et al. | |
| 7,959,645 B2 | | 6/2011 | WasDyke et al. | |
| 7,959,646 B2 | | 6/2011 | Huter et al. | |
| 7,967,838 B2 | | 6/2011 | Chanduszko et al. | |
| 7,972,353 B2 | | 7/2011 | Hendriksen et al. | |
| 7,972,355 B2 | | 7/2011 | Bales | |
| 7,993,362 B2 | | 8/2011 | Lowe et al. | |
| 7,998,164 B2 | | 8/2011 | Saholt et al. | |
| 8,025,675 B2 | | 9/2011 | Shirley et al. | |
| 8,029,529 B1 | | 10/2011 | Chanduszko | |
| 8,043,322 B2 | | 10/2011 | Hendriksen et al. | |
| 8,043,323 B2 | | 10/2011 | Holzer et al. | |
| 8,048,103 B2 | | 11/2011 | Salahieh | |
| 8,052,713 B2 | | 11/2011 | Khosravi et al. | |
| 8,057,507 B2 | | 11/2011 | Horan et al. | |
| 8,062,324 B2 | | 11/2011 | Shimon et al. | |
| 8,062,326 B2 | * | 11/2011 | McGuckin, Jr. | A61F 2/01 606/200 |
| 8,062,327 B2 | | 11/2011 | Chanduszko et al. | |
| 8,062,328 B2 | | 11/2011 | Hallisey | |
| 8,070,769 B2 | | 12/2011 | Broome | |
| 8,080,033 B2 | | 12/2011 | WasDyke | |
| 8,092,484 B2 | | 1/2012 | Kashkarov et al. | |
| 8,092,485 B2 | | 1/2012 | Lapid | |
| 8,092,486 B2 | | 1/2012 | Berrada et al. | |
| 8,092,487 B2 | | 1/2012 | Streeter et al. | |
| 8,100,936 B2 | * | 1/2012 | McGuckin, Jr. | A61F 2/01 606/200 |
| 8,105,349 B2 | | 1/2012 | Hendriksen et al. | |
| 8,118,828 B2 | | 2/2012 | Cartier et al. | |
| 8,133,251 B2 | | 3/2012 | Ravenscroft et al. | |
| 8,133,253 B2 | | 3/2012 | Bosma et al. | |
| 8,152,833 B2 | | 4/2012 | Zaver et al. | |
| 8,162,970 B2 | | 4/2012 | Gilson et al. | |
| 8,162,972 B2 | | 4/2012 | McGuckin, Jr. et al. | |
| 8,167,901 B2 | | 5/2012 | Hendriksen et al. | |
| 8,211,140 B2 | | 7/2012 | McGunkin, Jr. et al. | |
| 8,226,679 B2 | | 7/2012 | Johnson et al. | |
| 8,231,649 B2 | | 7/2012 | Petersen | |
| 8,231,650 B2 | | 7/2012 | Cully et al. | |
| 8,231,651 B2 | | 7/2012 | Tsugita | |
| 8,246,648 B2 | | 8/2012 | Tekulve | |
| 8,246,650 B2 | | 8/2012 | Osborne | |
| 8,246,651 B2 | | 8/2012 | Hendriksen et al. | |
| 8,252,017 B2 | | 8/2012 | Paul, Jr. et al. | |
| 8,267,954 B2 | | 9/2012 | Decant, Jr. et al. | |
| 8,273,099 B2 | | 9/2012 | DiMatteo | |
| 8,277,479 B2 | | 10/2012 | Messal et al. | |
| 8,282,668 B2 | | 10/2012 | McGuckin, Jr. et al. | |
| 8,303,618 B2 | | 11/2012 | Daniel et al. | |
| 8,317,818 B2 | | 11/2012 | Kashkarov et al. | |
| 8,317,819 B2 | | 11/2012 | Kusleika | |
| 8,328,842 B2 | | 12/2012 | Brady | |
| 8,333,785 B2 | | 12/2012 | Chanduszko et al. | |
| 8,353,926 B2 | | 1/2013 | Silver | |
| 8,361,103 B2 | | 1/2013 | Weaver et al. | |
| 9,034,006 B2 | * | 5/2015 | Quinn | A61B 17/12122 606/200 |
| 2002/0116024 A1 | * | 8/2002 | Goldberg | A61F 2/01 606/200 |
| 2002/0193828 A1 | * | 12/2002 | Griffin | A61F 2/01 606/200 |
| 2003/0109897 A1 | * | 6/2003 | Walak | A61F 2/01 606/200 |
| 2004/0073252 A1 | * | 4/2004 | Goldberg | A61F 2/01 606/200 |
| 2004/0193209 A1 | * | 9/2004 | Pavcnik | A61F 2/01 606/200 |
| 2004/0230220 A1 | * | 11/2004 | Osborne | A61F 2/01 606/200 |
| 2005/0131452 A1 | * | 6/2005 | Walak | A61F 2/01 606/200 |
| 2005/0165442 A1 | * | 7/2005 | Thinnes, Jr. | A61F 2/01 606/200 |
| 2005/0222604 A1 | * | 10/2005 | Schaeffer | A61F 2/01 606/200 |
| 2005/0251199 A1 | * | 11/2005 | Osborne | A61F 2/01 606/200 |
| 2005/0267513 A1 | | 12/2005 | Osborne et al. | |
| 2005/0267514 A1 | | 12/2005 | Osborne et al. | |
| 2005/0288704 A1 | * | 12/2005 | Cartier | A61F 2/01 606/200 |
| 2006/0058832 A1 | * | 3/2006 | Melzer | A61F 2/01 606/200 |
| 2006/0069406 A1 | | 3/2006 | Hendriksen et al. | |
| 2006/0079928 A1 | * | 4/2006 | Cartier | A61F 2/01 606/200 |
| 2006/0178695 A1 | * | 8/2006 | Decant, Jr. | A61B 5/02007 606/200 |

(56) References Cited

U.S. PATENT DOCUMENTS

| | | | |
|---|---|---|---|
| 2007/0032816 A1* | 2/2007 | O'Connell | A61F 2/01 606/200 |
| 2007/0173885 A1* | 7/2007 | Cartier | A61F 2/01 606/200 |
| 2007/0198050 A1* | 8/2007 | Ravenscroft | A61F 2/01 606/200 |
| 2007/0203520 A1* | 8/2007 | Griffin | A61F 2/01 606/200 |
| 2008/0221609 A1* | 9/2008 | McGuckin | A61F 2/01 606/200 |
| 2009/0076585 A1* | 3/2009 | Hendriksen | A61F 2/95 623/1.12 |
| 2015/0305849 A1* | 10/2015 | Forber | A61F 2/01 606/200 |

FOREIGN PATENT DOCUMENTS

| | | |
|---|---|---|
| WO | WO 2004/049953 | 6/2004 |
| WO | WO 2005/072645 | 8/2005 |
| WO | WO 2005/102210 | 11/2005 |
| WO | WO 2005/102211 | 11/2005 |
| WO | WO 2005/102212 | 11/2005 |
| WO | WO 2005/102213 | 11/2005 |
| WO | WO 2005/102214 | 11/2005 |
| WO | WO 2006/036867 | 4/2006 |

* cited by examiner

FILTER DEVICE, SYSTEM, AND METHOD

CROSS-REFERENCE TO RELATED APPLICATIONS

This application claims the benefit of U.S. Provisional Application No. 61/885,210 filed on Oct. 1, 2013, entitled "FILTER DEVICE, SYSTEM, AND METHOD," the entire contents of which are incorporated herein by reference.

FIELD OF THE INVENTION

The present invention relates to medical devices. More particularly, the invention relates to a removable vena cava clot filter having wings for limiting tilting that can be percutaneously placed in and removed from the vena cava of a patient.

BACKGROUND OF THE INVENTION

Filtering devices that are percutaneously placed in the vena cava have been available for over thirty years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

After deployment of a generally conical filter in a patient, the filter may eventually end up in a tilted position. Proliferating intimal cells begin to accumulate around the filter parts which contact the wall of the vessel. After a length of time, such ingrowth prevents removal of the filter without risk of trauma so that the filter is permanently left in the patient.

Moreover, conventional filters commonly become off-centered or tilted with respect to the hub of the filter and the longitudinal axis of the vessel in which it has been inserted. As a result, the filter including the hub and the retrieval hook engage the vessel wall along their lengths and potentially become endothelialized therein. As a result, the filter becomes a permanent implant in a shorter time period than otherwise.

Further improvements may be made related to the retrieval of vena cava filters.

SUMMARY

One embodiment of the present invention generally provides a removable vena cava filter configured for reducing the risk of a tilted implantation. A filter for capturing blood clots in a body lumen includes a single hub defining a longitudinal axis extending through the single hub, a plurality of filter struts attached to the hub and extending longitudinally and radially away from the hub in a first longitudinal direction, a plurality of wire loops attached to the hub and extending longitudinally and radially away from the hub in a second longitudinal direction opposite the first longitudinal direction, wherein each wire loop of the plurality of wire loops includes first and second ends each attached to the single hub and a bent portion extending between the first and second ends to define the wire loop.

In another form, a method for retrieving a filter device comprises the steps of introducing a retrieval sheath having a lumen and proximal and distal ends into a body lumen; translating a snaring mechanism relative to the sheath in a distal direction through the lumen of the sheath; positioning the snaring mechanism distally beyond the distal end of the sheath; engaging the snaring mechanism with a hook member of a filter device; and translating the retrieval sheath relative to the filter device and the snaring mechanism to load the filter device and the snaring mechanism into the retrieval sheath lumen.

Further details and benefits of the present invention become apparent from the following description of drawings illustrating preferred embodiment of the invention. The drawings are presented herein solely for illustrative purposes and are not intended to limit the scope of the present invention.

DETAILED DESCRIPTION OF THE DRAWINGS

Figure 1:
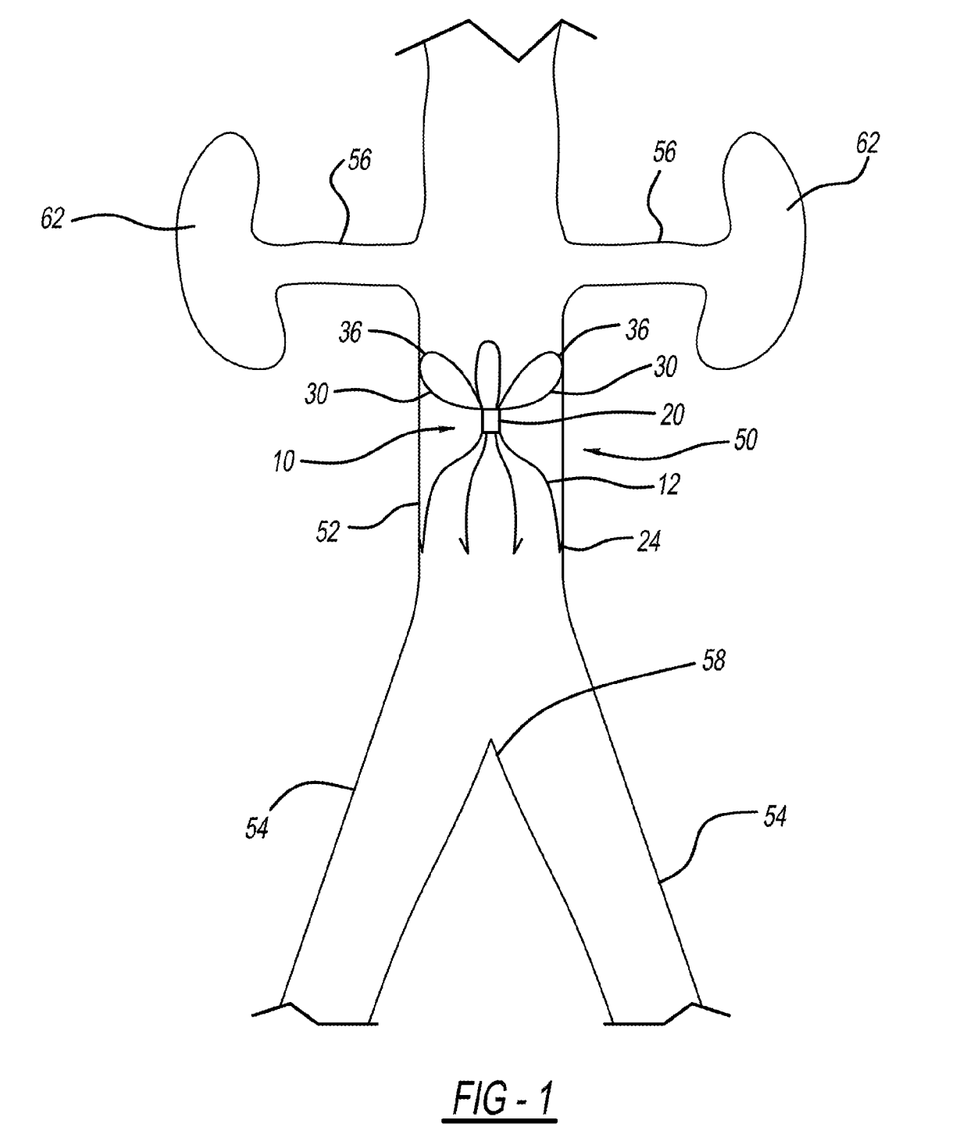
FIG. 1 is a schematic view of a filter device having a plurality of filter struts and a plurality of wire loops shown deployed within a body vessel.

In accordance with one embodiment of the present invention, FIG. 1 illustrates a vena cava filter 10 implanted in the vena cava 50 for the purpose of lysing or capturing thrombi carried by the blood flowing through the iliac veins 54 toward the heart and into the pulmonary arteries. As shown, the iliac veins merge at juncture 58 into the vena cava 50. The renal veins 56 from the kidneys 62 join the vena cava 50 downstream of juncture 58. The portion of the vena cava 50, between the juncture 58 and the renal veins 56, defines the inferior vena cava 52 in which the vena cava filter 10 has been percutaneously deployed through one of the femoral veins. Preferably, the vena cava filter 10 has a length smaller than the length of the inferior vena cava 52. If the lower part of the filter extends into the iliac veins, filtering effectiveness will be compromised and if the filter wires cross over the origin of the renal veins the filter wires might interfere with the flow of blood from the kidneys.

Figure 2:
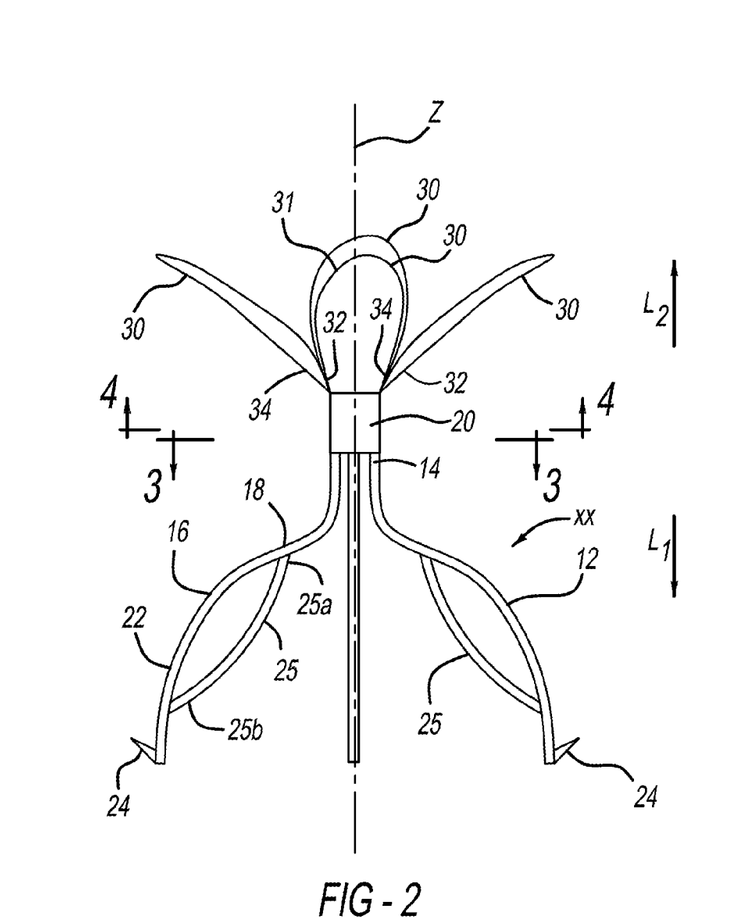
FIG. 2 is a schematic front view of the filter device.

This embodiment of the present invention will be further discussed with reference to FIGS. 1-13, in which filter 10 is shown. FIG. 2 illustrates the filter 10 in an expanded state and comprising a plurality of filter struts 12 each having first ends 14 that emanate from a hub 20. While four struts 12 are illustrated, it will be appreciated that other quantities of struts can also be used to suit the needs of the user. The hub 20 attaches by crimping the first ends 14 of the struts 12 together in a compact bundle along a central or longitudinal axis Z of the filter 10. The hub 20 has a minimal diameter for the size of wire used to form the struts.

Preferably, the filter struts 12 are formed of a superelastic material, stainless steel wire, Nitinol, cobalt-chromium-nickel-molybdenum-iron alloy, or cobalt chrome-alloy or any other suitable superelastic material that will result in a self-opening or self-expanding filter. In this embodiment, the filter struts 12 are preferably formed from wire having a round cross-section with a diameter of at least about 0.015 inches. Of course, it is not necessary that the struts 12 have a round or near round cross-section. For example, the struts 12 could take on any shape with rounded edges to maintain non-turbulent blood flow therethrough. In another form, the struts 12 could have non-rounded edges.

As shown in FIG. 2, each strut 12 includes an arcuate segment 16 having a soft S-shape. Each arcuate segment 16 is formed with a first curved portion 18 that is configured to softly bend away from the longitudinal or central axis Z of the filter 10 and a second curved portion 22 that is configured to softly bend toward the longitudinal axis of the filter 10. Due to the soft bends of each arcuate segment 16, a prominence or a point of inflection on the primary strut 12 is substantially avoided to aid in non-traumatically engaging the vessel wall.

As shown in FIG. 2, the struts 12 terminate at anchor hooks 24 that will anchor in the vessel wall when the filter 10 is deployed at a delivery location in the blood vessel, as shown in FIGS. 1, 7, and 10-12. The struts 12 are configured to move between an expanded and deployed state or configuration for engaging the anchor hooks 24 with the blood vessel and a collapsed or compressed delivery state or configuration for use primarily during filter delivery and subsequent filter retrieval. In the expanded state, each arcuate segment 16 extends arcuately outward along a longitudinal axis Z from the end 14 to the anchor hook 24. As shown in the bottom view of FIG. 3, in this embodiment, the struts 12 do not have any curves in the circumferential direction and avoid entanglement with other struts 12. The extension of the struts 12 can be described as extending both longitudinally and radially in a first longitudinal direction.

Figure 3:
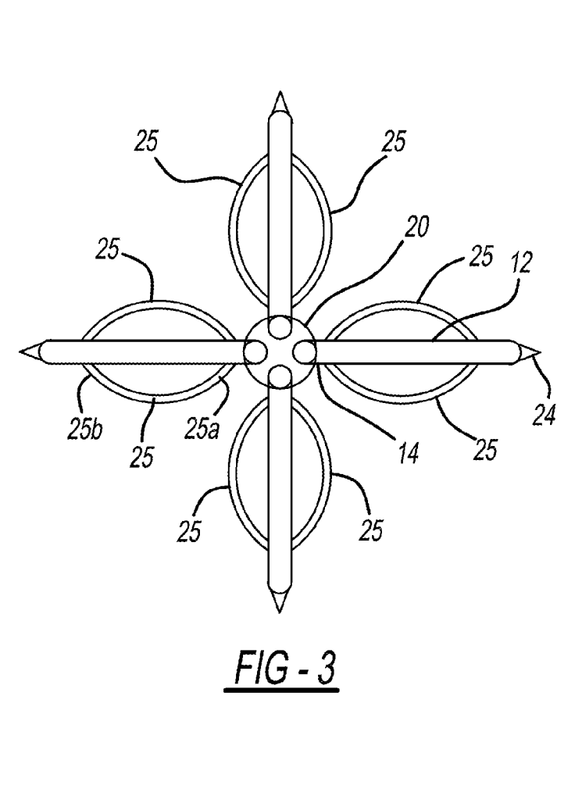
FIG. 3 is a top cross-sectional view taken along the line 2-2 of FIG. 1; showing the filter struts.

With reference to FIGS. 2 and 3, the filter 10 can also include secondary struts 25 that are attached to the filter struts 12. More specifically, each of the secondary struts 25 include a first end 25a and a second end 25b. The first and second ends 25a and 25b are connected to the filter strut 12 to provide support. The secondary struts 25 are disposed radially inward from the filter struts 12, as shown in FIG. 2. Each filter strut 12 can include a pair of secondary struts 25, as shown in FIG. 3, that extend circumferentially away from the filter strut 12. The secondary struts 25 will generally not become tangled because both ends 25a and 25b are connected to the filter strut 12. Of course, the filter struts 12 can also be free from the secondary struts 25, or other types of secondary struts, such as those known in the art, could also be used to provide support to the filter struts 12.

The struts 12 each extend in a first longitudinal direction L1 along the Z-axis from the hub 20 while also extending radially away from the hub 20. While struts 12 have been described as having a curved shape, it will be appreciated that other shapes could also be used, such as a straight shape, or a bent shape. Regardless of the shape of the strut 12, the struts 12 will ultimately extend radially outward and in the first longitudinal direction L1 to form a cup-like filtering shape.

When the filter 10 is deployed in a blood vessel, the anchor hooks 24 engage the walls of the blood vessel to secure the filter 10 in the blood vessel, as shown in FIGS. 1, 7, and 10-12. The anchor hooks 24 prevent the filter 10 from migrating from the delivery location in the blood vessel where it has been deposited. The struts 12 are shaped and dimensioned such that, when the filter 10 is freely expanded, the filter 10 has a diameter of between about 25 mm and 45 mm and a length of between about 3 cm and 7 cm. For example, the filter 10 may have a diameter of about 35 mm and a length of about 5 cm. The struts 12 have sufficient spring strength that, when the filter 10 is deployed, the anchor hooks 24 will anchor into the vessel wall.

In this embodiment, the filter 10 includes a plurality of loops 30 each being defined by a wire 31 having a first end 32 and a second end 34, both of which are attached to the hub 20 as shown in FIGS. 2 and 4-8. The connected first and second ends 32, 34 of the wire 31 define the loop 30 in a closed form, such that the loops 30 do not have a free end. However, it will be appreciated that one or both of the ends 32, 34 could extend past the hub 20 such that they would be free, but the connection at the hub 20 of both ends 32, 34 will still define the loop 30 in a closed form. In the embodiment shown in FIG. 2, four loops 30 emerge from the hub 20 at an axial side opposite the filter struts 12 and in a second longitudinal direction L2. In the following, the axial side of the hub 20 from which the filter struts 12 extend will be called primary side, and the axial side of the hub 20 from which the loops 30 extend will be called secondary side.

While the described embodiment includes four loops 30, the plurality of loops 30 can also comprise a quantity of loops that is greater than or less than the described four loop arrangement. For example, a pair of loops 30 could be used, or five loops 30 could be used. The loops 30 are preferably arranged and oriented such that when viewed axially, the loops 30 will appear to form a cloverleaf or flower petal shape.

Figure 4:
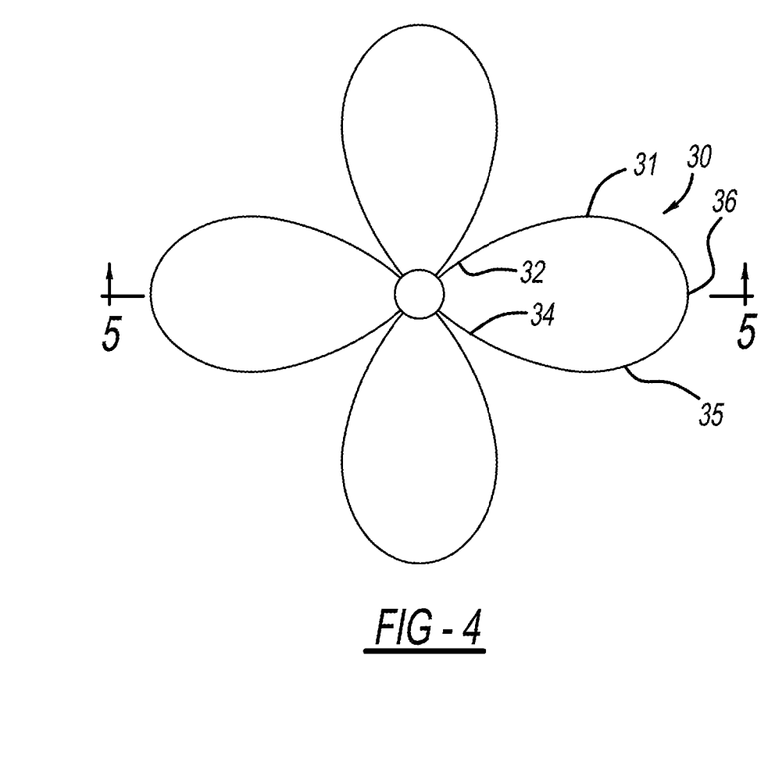
FIG. 4 is a bottom cross-sectional view taken along the line 4-4, showing the wire loops.
Figure 5:
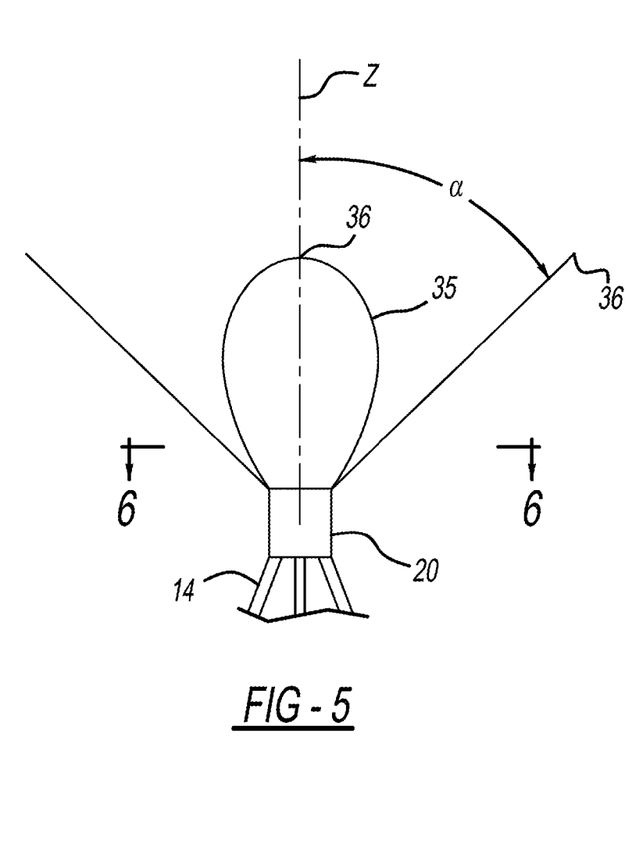
FIG. 5 is a front cross-sectional view taken along the line 5-5 of FIG. 4, showing the wire loops.
Figure 7:
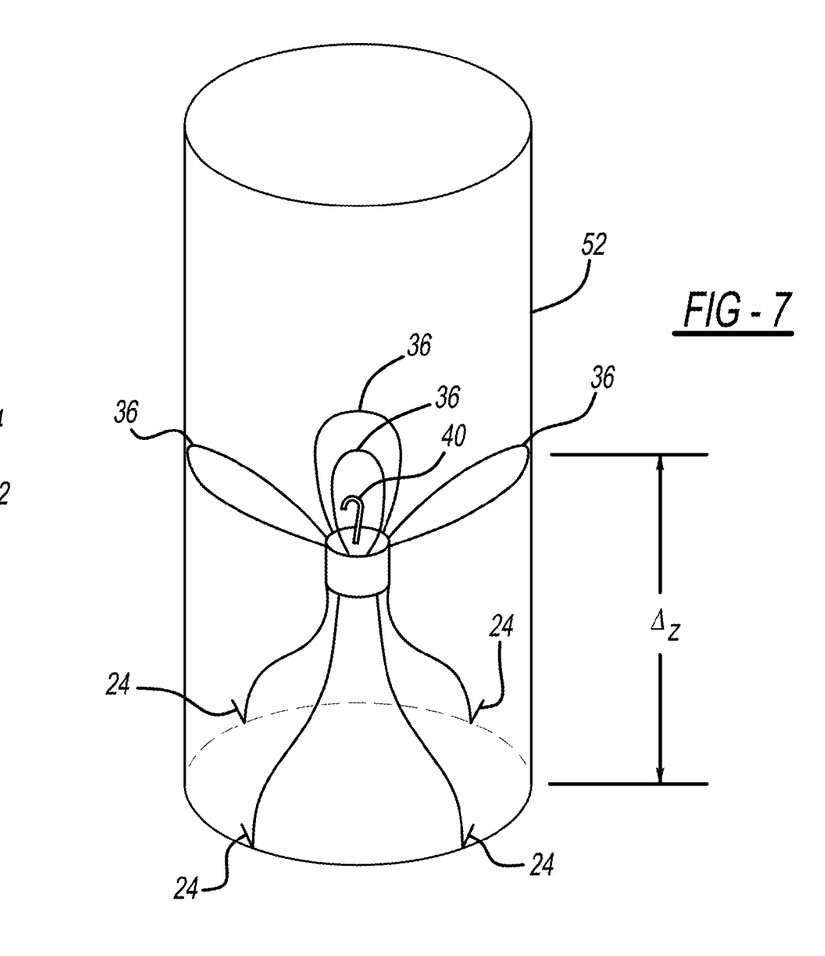
FIG. 7 is a schematic perspective view showing the filter device deployed.

The loops 30 extend longitudinally away from the hub in the second longitudinal direction L2 that is opposite the first longitudinal direction L1, as well as extending radially away from the hub 20. More specifically, the wire 31 extends from its first end 32 connected to the hub 20 longitudinally and radially away from the hub. The wire 31 includes a curved middle portion 35 that curves back toward the hub 20. The curved middle portion 35 defines an apex 36 at its outermost point from the hub 20, as shown in FIG. 4. The wire 31 curves back toward the hub 20, where the second end 34 is connected to the hub 20 to define the loop 30 in a closed form. The apex 36 is the point of the loop 30 that is preferably in contact with the body lumen to align the filter 10 therein and prevent the filter 10 from becoming tilted, as shown in FIG. 7. In other words, the loops 30 have an expanded or deployed state or configuration, in which each of the loops 30 extend at an angle a away from the longitudinal axis Z to form a generally conical shape, where the angle a corresponds to the angle of the generally conical shape, as shown in FIG. 5. In one form, the angle a can be approximately 45 degrees; however, other angles could also be used, such as an angle between about 30 degrees and 60 degrees. While the loops 30 have been described as forming a generally conical shape, it will be appreciated that individual ones of the loops could be slightly tilted such that the shape is not exactly conical.

Figure 6:
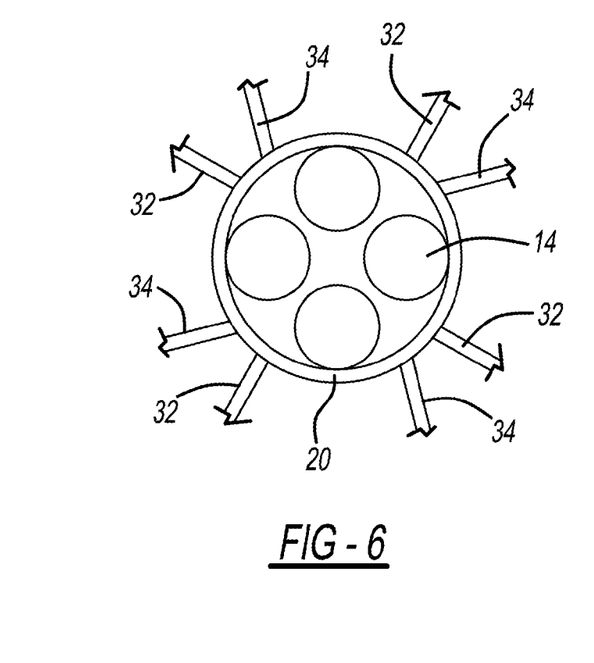
FIG. 6 is a top cross-sectional view taken along the line 6-6 of FIG. 5, showing a single hub connecting the filter struts and the wire loops.

With reference to FIG. 6, the hub 20 is attached to the connected ends 32 and 34 of the loops 30 and the connected ends 14 of the filter struts 12. The connection between the hub 20 and ends 14 and 32, 34 may, for example, be accomplished by crimping, by laser welding, or any other suitable method creating a durable connection. In this embodiment, each filter strut 12 has its connected ends 14 arranged side-by-side and distributed around the circumference of the hub 20. The ends 32 and 34 of the loops 30 are preferably soldered or welded to the hub 20 and evenly spaced about the circumference of the hub 20 as well and preferably at circumferential locations between the ends 14 of the filter struts 12. Of course, different quantities of loops 30 and filter struts 12 could be used, so other arrangements of the ends 14, 32, and 34 could be used. The loops 30 extend from the connected ends 32, 34 to longitudinally align the filter 10 in the expanded state in the blood vessel as illustrated n FIG. 1.

Thus, both the filter struts 12 and the loops 30 extend radially outward, but on opposite longitudinal sides of the hub 20 to align the filter 10 longitudinally within the blood vessel. The connection of the loops 30 and filter struts 12 is accomplished by connecting them to the single hub 20.

The loops 30 may be made from the same type of material as the filter struts 12. However, the loops 30 may have a smaller diameter than the filter struts 12, e.g. at least about 0.012 inches. The hub 20 is preferably made of the same material as the filter struts 12 and loops 30 to minimize the possibility of galvanic corrosion or molecular changes in the material due to welding.

The filter struts 12 and loops 30 may be formed from any suitable material that will result in a self-opening or self-expanding filter 10, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives.

In one embodiment, the transition temperature is chosen to be slightly below normal body temperature of humans, which is about 98.6° F. Thus, when the filter 10 is deployed in the vena cave 52 and exposed to normal body temperature, the alloy of the struts 12 and 30 will transform to austenite, that is, the remembered state, which for the present invention is an expanded configuration when the filter 10 is deployed in the blood vessel. To remove the filter 10, the filter 10 is cooled to transform the material to martensite which is more ductile than austenite, making the struts 12 and 30 more malleable. As such, the filter 10 can be more easily collapsed and pulled into the sheath for removal.

In other embodiments, both the filter struts 12 and the loops 30 are made from Nitinol with a transition temperature that is above normal body temperature of humans, which is about 98.6° F. Thus, when the filter is deployed in the vena cava and exposed to normal body temperature, the struts are in the martensitic state so that the struts are sufficiently ductile to bend or form into a desired shape, which for the present invention is an expanded configuration. To remove the filter, the filter is heated to transform the alloy to austenite so that the filter becomes rigid and returns to a remembered state, which for the filter is a collapsed configuration.

Notably, other materials allowing for a delivery and removal of the filter 10 by elastic deformation are well within the scope of the present invention.

When freely expanded, the loops 30 will expand radially outward to a diameter of about 25 mm to 45 mm. Generally, the expanded diameter of the loops 30 is similar to the expanded diameter of the filter struts 12 in the sense that the diameters are chosen relative to each other to provide support for identical vessel diameters. Of course, these dimensions are exemplary, and other expanded diameters of both the filter struts 12 and the loops 30 could also be used to suit different sized anatomy. In that regard, anatomy that differs in diameter at different axial locations would result in different expanded diameters of the loops 30 and the filter struts 12 because the engagement points thereof are at different axial locations.

The loops 30 function to stabilize the position of the filter 10 about the center of the blood vessel in which it is deployed. As evident from FIG. 2, each of the loops 30 includes the apex 36 of the curved portion 35. These apexes 36 engage the vessel wall of the vena cava after deployment as can be seen in FIGS. 1, 7, and 10-12. Thus, the loops 30 contact the vessel wall without perforating it.

As a result, the filter 10 has two sets of wires engaging the vessel wall of the blood vessel in locations that are longitudinally apart by an offset Az, as shown in FIG. 7. The offset Az is greater than the longitudinal distance of the anchor hooks 24 from the hub 20. Compared to smaller offsets, the larger Az has the advantage that a deformation or displacement of a strut 12 or loop 30 has a smaller influence on the alignment angle of the longitudinal axis Z relative to the direction of the inferior vena cava 52. Thus, the filter alignment becomes more robust.

As briefly indicated above, the length of the filter 10 in the compressed or collapsed delivery state is defined by the sum of the lengths of the filter struts 12 and of the loops 30 when aligned longitudinally. In the expanded or deployed state, the length of the filter 10 is approximately defined by the sum of the longitudinal component of the filter struts 12 and the loops 30. The length of the filter 10 in the expanded state is shorter than the length in the compressed state because the struts 12 and loops 30 are directed radially as well as longitudinally.

In this embodiment, the diameter of the hub 20 is defined by the size of a bundle containing the filter struts 12 on the primary side or the loops 30 on the secondary side. In another embodiment, the struts 12 and loops 30 are both connected within the hub 20 and combine to define the diameter of the hub 20, but the struts 12 and loops 30 do not necessarily overlap each other along the longitudinal axis Z. Thus, the diameter of the hub 20 is determined by the point along the axis Z that has the greatest lateral buildup of struts 12, loops 30, or both. The number of struts 12 and loops 30 can vary according to different embodiments, so the diameter of the hub 20 can change as the quantities of the struts 12 and loops 30 increase or decrease. Thus, the diameter of the hub 20 corresponds to a cross-section that accommodates the larger one of the cross-sections of the strut or loop bundles.

In this embodiment, each arcuate segment 16 has a thickness of at least about 0.015 inch and a tensile strength of between about 285,000 pounds per square inch (psi) and 330,000 psi. Each anchor hook 24 is integral with the arcuate segment 16 and has the thickness and the tensile strength of the arcuate segment 16. Each wire 31 defining the loops 30 has a thickness of at least about 0.012 inch and a tensile strength of between about 285,000 psi and 330,000 psi.

In this embodiment of the present invention, it is to be noted that the filter 10 may be delivered by any suitable introducer tube. However, it is preferred that the introducer tube has an inside diameter of between about 4.5 French and 16 French, and more preferably between about 6.5 French and 14 French.

For example, the filter 10 may be inserted from the femoral side through the proximal end of a delivery tube with the secondary side leading. During deployment, the loops 30 expand first to centralize or balance the filter 10 within the vessel according to the shape memory characteristics described above. When the ends of the loops 30 emerge from the distal end of the delivery tube, the loops 30 expand and open outwardly from the compressed delivery state into the expanded deployed state as shown in FIGS. 1, 7, 10-12. The filter 10 may then pushed further by a pusher wire until it is fully deployed. Alternatively, the delivery tube may be withdrawn to allow the filter struts 12 to expand radially into engagement with the body vessel as shown in FIGS. 1, 7, 10-12. Exposing the filter struts 12 will allow them to expand radially outward due to their shape memory characteristics described above. Other known methods for delivering and deploying a filter to a body vessel such as the vena cava can also be used to deliver the filter 10 into its engaged position with body vessel wall.

As shown in FIGS. 1, 7, 10-12, when the filter 10 is fully expanded in the vena cava, the anchor hooks 24 of the filter struts 12 and the apexes 36 of the loops 30 are in engagement with the vessel wall. The anchor hooks 24 of the filter struts 12 have anchored the filter 10 at the location of deployment in the vessel, preventing the filter 10 from moving with the blood flow through the vessel. The loops 30 reduce the risk of tilting by keeping the hub 20 centered within the body vessel. As a result, the filter 10 is supported by the plurality of struts 12 and the plurality of loops 30 that are spaced axially along the length of the filter 10 by offset Az (FIG. 7).

Figure 8:
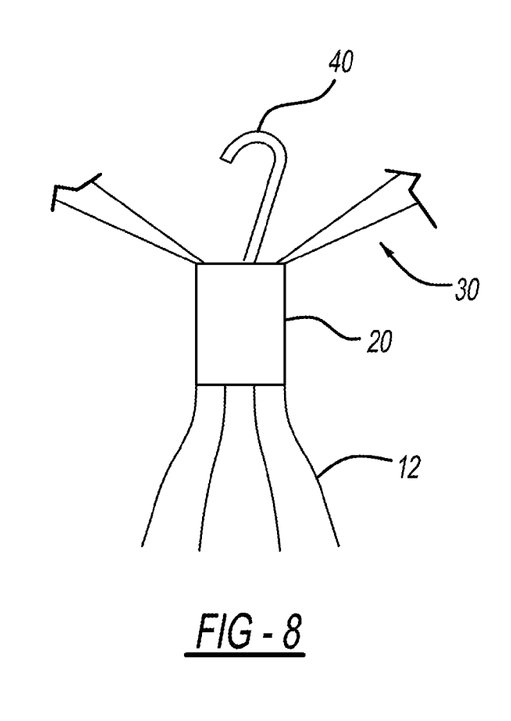
FIG. 8 is a front schematic view showing a hook member of the filter device.
Figure 9:
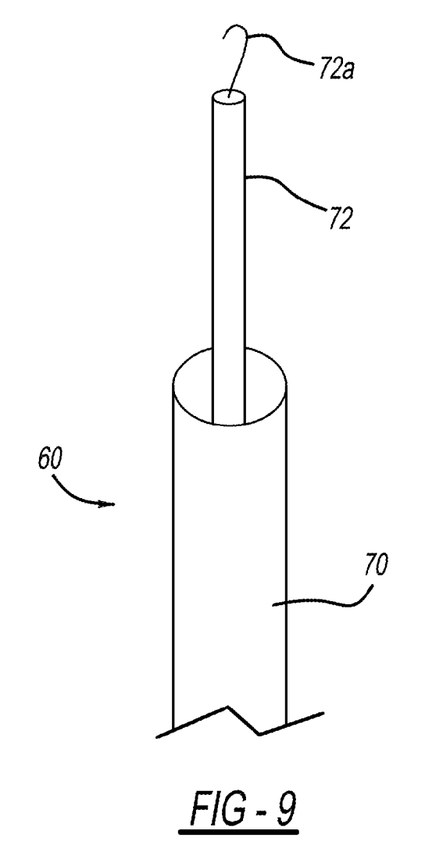
FIG. 9 is a schematic view of a retrieval device including a retrieval sheath and a snaring mechanism.

As shown in FIGS. 7 and 8, the filter 10 also includes a hook member 40 attached at the hub 20 and disposed generally at the longitudinal axis Z. The hook member 40 extends in same longitudinal direction as the loops 30, so that when the loops 30 are in the expanded state, the hook member 40 is disposed within the conical shape formed by the loops 30. The hook member 40 can be made from any rigid and biocompatible material, and will preferably not become substantially deformed upon contact with a snaring device. Various other types of hook members are known and can be used in place of the above described and shown hook member 40. In another form, the hook member 40 can extend in the opposite direction, that is, in the same longitudinal direction as the struts 12. In yet another form, the filter 10 can include a pair of hook members 40 extending on both sides. The location of the hook member 40 on the filter 10 can be selected to allow for retrieval of the device from a preferred direction.

The anti-tilting design of the filter 10, described above, will preferably prevent the hook member 40 from engaging the vessel wall while the filter 10 is deployed, preventing the hook member 40 from becoming embedded in the vessel wall. With the hook member 40 remaining free from engagement with the vessel wall and tissue ingrowth, the filter 10 can be more easily retrieved using a retrieval device.

With reference to FIGS. 9-13, the hook member 40 can be used in combination with a retrieval device 60 to remove the filter 10 from the body when desired. The retrieval device 60 includes a removal sheath 70 and a snaring mechanism 72 that is longitudinally translatable relative to the sheath 70. As will be described in further detail below, the snaring mechanism 72 can be exposed from the sheath 70 to engage the hook member 40 of the filter device 10 so that the filter device 10 can be retrieved and moved into the sheath 70. The snaring mechanism 72 can include a head portion 72a that is configured to cooperate with the hook member 40 such that the hook member 40 and the snaring mechanism 72 will become coupled. The head portion 72a can have any structure that will couple with the hook member 40, such as a hook shape, a plurality of loops, or the like.

Figure 10:
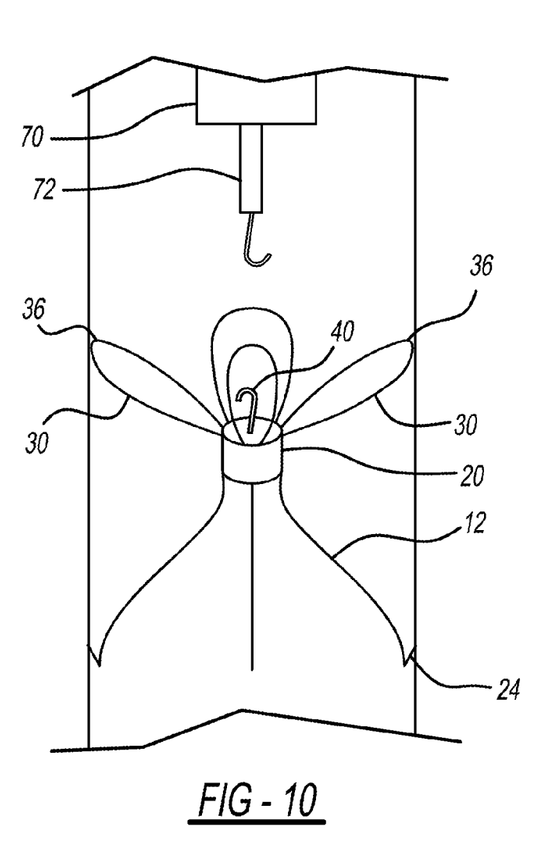
FIGS. 10-13 are schematic views illustrating a retrieval method of the filter device from the body vessel using the retrieval device.

With reference to FIG. 10, to retrieve the filter 10, the snaring mechanism 72 can be exposed from the sheath 70, either by retracting the sheath 70 relative to the snaring mechanism 72 or by advancing the snaring mechanism 72 relative to the sheath 70. It will be appreciated that any reference to exposing the snaring mechanism 72 can include one or both of these methods.

Figure 11:
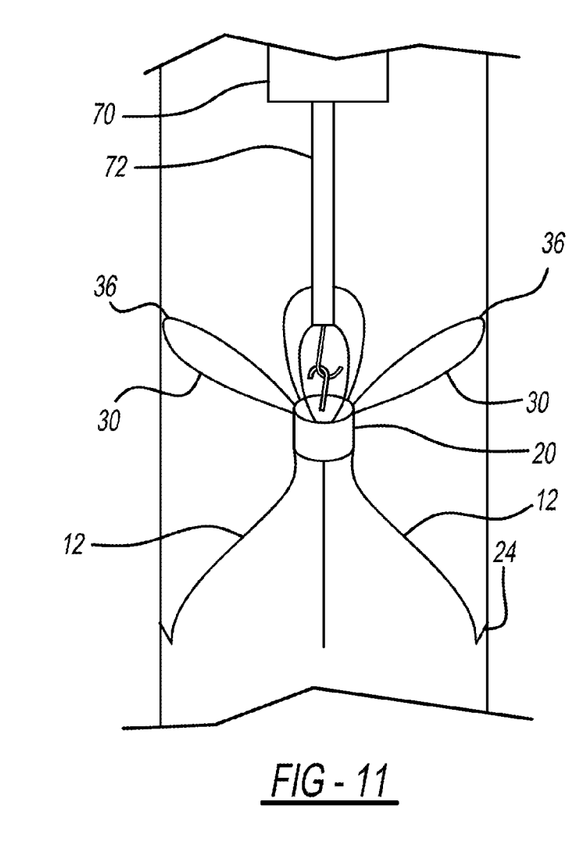

With reference to FIG. 11, with the snaring mechanism 72 exposed, the snaring mechanism 72 can be advanced into engagement with the hook member 40 of the filter 10, thereby coupling the filter 10 to the retrieval device 60. The sheath 70 can then be translated toward the filter 10, where the filter 10 will be enveloped by the sheath 70. When the sheath 70 contacts the filter 10, the snaring mechanism 72 will prevent the filter 10 from being pushed away and will allow the sheath 70 to receive the filter 10.

Figure 12:
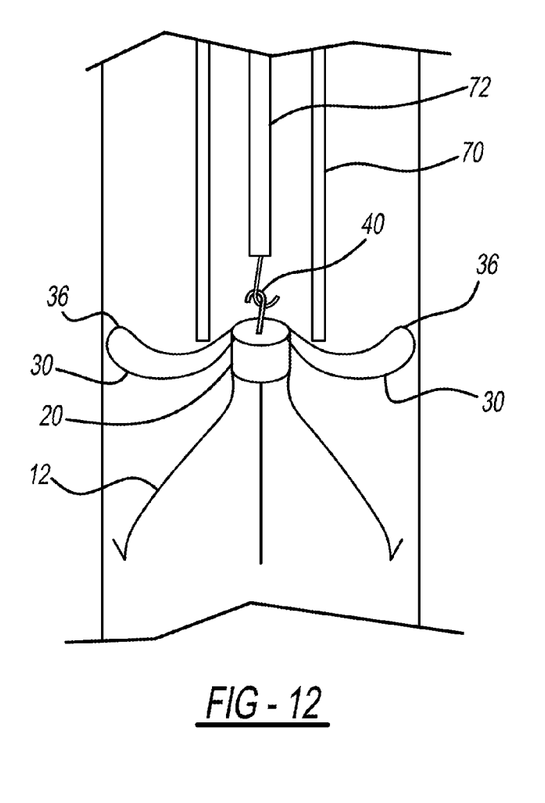
Figure 13:
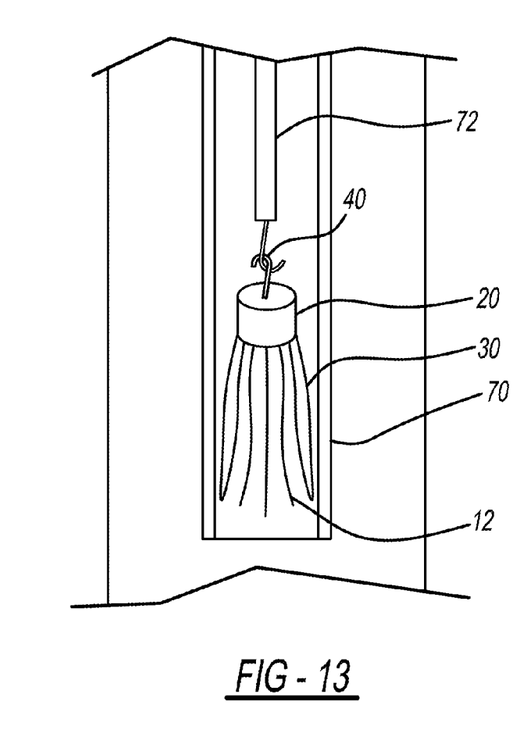

As shown in FIGS. 12 and 13, with the snaring mechanism 72 coupled to the filter 10, the filter 10 can be retrieved by using the sheath 70. The sheath 70 is advanced toward the filter 10. The snaring mechanism 72 is held generally stationary, such that the sheath 70 advances relative thereto.

As the sheath 70 advances toward the filter 10, the sheath 70 will contact the plurality of loops 30 prior to the filter struts 12. The wire 31 defining the loops 30, being relatively thin, will deform in response to the sheath 70 making contact with the distal end of the sheath 70. The diameter of the sheath 70 is smaller than the diameter of the body vessel, so the distal end of the sheath 70 will contact the loops 30 circumferentially and at a radial location between the vessel wall and the longitudinal axis Z.

With the sleeve 70 being advanced and in contact with the loops 30, the sleeve will continue to be advanced, forcing the loops 30 in the direction of the filter struts 12, causing the loops 30 to bend around the distal end of the sleeve 70. The loops 30 will bow circumferentially to accommodate the shorter length caused by forcing them downward.

As the sleeve 70 continues being advanced, the loops 30 will fold over and become overlaid across the filter struts 12 (FIG. 13), thereby being arranged in the same direction as the filter struts 12. The sleeve 70 will continue advancing, enveloping the loops 30 and the filter struts 12. More specifically, the sleeve 70 will force the filter struts 12 radially inward as it advances, detaching the anchor ends 24 from the vessel wall.

With the filter 10 received within the sleeve 70, the filter 10, snaring mechanism 72, and sleeve 70 can be retracted from the body.

The above retrieval method is described with reference to snaring the filter 10 from the side having the loops 30 with a reduced number of components relative to known filter retrieval methods. However, it will be appreciated that known filter retrieval methods could also be used to retrieve the filter 10 if desired. For example, a method where the filter 10 is retrieved from the side of the filter 10 having the struts 12 could be performed where an alternative snaring device could be used that compresses the filter struts 12 radially inward such that they can be received by a sheath.

While the present invention has been described in terms of preferred embodiments, it will be understood, of course, that the invention is not limited thereto since modifications may be made to those skilled in the art, particularly in light of the foregoing teachings.

What is claimed is:

1. A filter for capturing blood clots in a body lumen, the filter comprising:
    a single hub defining a longitudinal axis extending through the single hub;
    a plurality of filter struts attached to the hub and extending longitudinally and radially away from the hub in a first longitudinal direction;
    a plurality of wire loops attached to the hub and emerging from the hub longitudinally and radially from the hub in a second longitudinal direction opposite the first longitudinal direction, wherein each wire loop of the plurality of wire loops consists of a first end attached to the single hub, a second end, attached to the single hub, and a bent portion extending from the first end to the second end to define the wire loop, the bent portion having an outermost point forming an apex, at which the bent portion extending from the first end curves back and extends back to the second end, wherein the plurality of loops from the hub to the apices forms a generally conical shape in a deployed configuration, in which the plurality of wire loops is radially expanded, wherein each of the apices is part of the conical shape.

2. The filter of claim 1, wherein the plurality of filter struts have a delivery configuration and a deployed configuration, the plurality of filter struts are radially compressed in the delivery configuration, and the plurality of filter struts are radially expanded relative to the delivery configuration when in the deployed configuration.

3. The filter of claim 1, wherein each of the filter struts of the plurality of filter struts includes a secondary strut attached thereto.

4. The filter of claim 3, wherein the secondary strut comprises a pair of second struts.

5. The filter of claim 3, wherein the secondary strut has first and second ends each attached to the primary strut.

6. The filter of claim 3, wherein the secondary strut is disposed radially inward from the primary strut.

7. The filter of claim 1 further comprising a hook attached to the hub.

8. The filter of claim 7, wherein the hook extends in the same longitudinal direction as the plurality of wire loops.

9. The filter of claim 1, wherein the plurality of wire loops has a delivery configuration, in which the plurality of wire loops is radially compressed.

10. The filter of claim 1, wherein each wire loop of the plurality of wire loops extends between 30 and 60 degrees away from the longitudinal axis when in the deployed configuration.

11. The filter of claim 1, wherein the plurality of wire loops are made of a shape memory material.

12. The filter of claim 1, wherein each wire loop of the plurality of wire loops have a thickness of about 0.012 inches.

13. The filter of claim 1, wherein the filter is adjustable into a retrieval state, where the plurality of wire loops are folded over the plurality of filter struts such that the plurality of filter struts and the plurality of wire loops extend in the same longitudinal direction.

14. A method for retrieving a filter device from a body lumen, the method comprising:
    introducing a retrieval sheath having a lumen and proximal and distal ends into a body lumen;
    translating a snaring mechanism relative to the sheath in a distal direction through the lumen of the sheath;
    positioning the snaring mechanism distally beyond the distal end of the sheath;
    engaging the snaring mechanism with a hook member of a filter device, wherein the filter device comprises a plurality of filter struts extending from a first end of a single hub in a first longitudinal direction and a plurality of wire loops emerging from a second end of the single hub, which is opposite the first end, in a second longitudinal direction opposite the first longitudinal direction and forming a generally conical shape when the filter device is in a deployed configuration, wherein each wire loop of the plurality of wire loops consists of a first end attached to the single hub, a second end, attached to the single hub, and a bent portion extending from the first end to the second end to define the wire loop;
    translating the retrieval sheath relative to the filter device and the snaring mechanism to load the filter device and the snaring mechanism into the retrieval sheath lumen,
    engaging the plurality of wire loops with the retrieval sheath, folding the plurality of wire loops over the plurality of filter struts such that the plurality or wire loops and the plurality of filter struts extend in the first longitudinal direction, and receiving the plurality of wire loops and the plurality of filter struts within the retrieval sheath lumen.

15. The method of claim 14, further comprising translating the snaring mechanism toward the hook member, wherein the snaring mechanism is disposed radially within the plurality of wire loops.

* * * * *